United States Patent
Schmidt et al.

(10) Patent No.: US 10,463,268 B2
(45) Date of Patent: Nov. 5, 2019

(54) SYSTEM AND METHOD FOR ACQUIRING PATIENT PHYSIOLOGICAL INFORMATION DURING AN MRI SCAN

(75) Inventors: Ehud Schmidt, Newton, MA (US);
Tsz-ho Tse, Lawrenceville, GA (US);
Charles Dumoulin, Cincinnati, OH (US)

(73) Assignees: THE BRIGHAM AND WOMEN'S HOSPITAL, Boston, MA (US);
CHILDREN'S HOSPITAL MEDICAL CENTER, Cincinnati, OH (US)

( * ) Notice: Subject to any disclaimer, the term of this patent is extended or adjusted under 35 U.S.C. 154(b) by 1770 days.

(21) Appl. No.: 14/110,967

(22) PCT Filed: Apr. 17, 2012

(86) PCT No.: PCT/US2012/033883
§ 371 (c)(1),
(2), (4) Date: Dec. 17, 2013

(87) PCT Pub. No.: WO2012/145285
PCT Pub. Date: Oct. 26, 2012

(65) Prior Publication Data
US 2014/0171783 A1    Jun. 19, 2014

Related U.S. Application Data

(60) Provisional application No. 61/478,281, filed on Apr. 22, 2011, provisional application No. 61/477,528, filed on Apr. 20, 2011.

(51) Int. Cl.
*A61B 5/055* (2006.01)
*A61B 5/0408* (2006.01)
(Continued)

(52) U.S. Cl.
CPC .......... *A61B 5/0408* (2013.01); *A61B 5/0402* (2013.01); *A61B 5/055* (2013.01);
(Continued)

(58) Field of Classification Search
CPC .............................. A61B 5/0408; A61B 5/055
See application file for complete search history.

(56) References Cited

U.S. PATENT DOCUMENTS

2004/0225210 A1    11/2004 Brosovich et al.
2005/0215886 A1    9/2005 Schmidt
(Continued)

FOREIGN PATENT DOCUMENTS

JP    2004329669 A    11/2004
WO    03100450 A1    12/2003
(Continued)

OTHER PUBLICATIONS

Dukkipati, et al., Electroanatomic Mapping of the Left Ventricle in a Porcine Model of Chronic Myocardial Infarction with Magnetic Resonance-Based Catheter Tracking, Circulation, 2008, 118:853-862.
(Continued)

*Primary Examiner* — Rochelle D Turchen
(74) *Attorney, Agent, or Firm* — Quarles & Brady LLP; Jack M. Cook

(57) ABSTRACT

A system and method for monitoring patient physiological information during an MRI scan sequence is provided. The system includes a monitoring device configured to sense physiological information from a patient. The physiological information may include electrocardiograph signals, electroanatomical mapping signals, or other information concerning a physiological condition of the patient. The system further includes a control circuit connected to receive signals
(Continued)

from the monitoring device and to coordinate output of the electrode during an MRI scan.

18 Claims, 4 Drawing Sheets

(51) Int. Cl.
    *G01R 33/567*     (2006.01)
    *A61B 5/00*     (2006.01)
    *A61B 5/0402*     (2006.01)
    *A61B 5/06*     (2006.01)
    *G01R 33/28*     (2006.01)

(52) U.S. Cl.
    CPC .......... *A61B 5/7217* (2013.01); *A61B 5/7285* (2013.01); *A61B 5/7289* (2013.01); *G01R 33/5673* (2013.01); *A61B 5/061* (2013.01); *G01R 33/285* (2013.01)

(56) References Cited

U.S. PATENT DOCUMENTS

| | | |
|---|---|---|
| 2006/0084849 A1 | 4/2006 | Newman et al. |
| 2006/0100506 A1 | 5/2006 | Halperin et al. |
| 2006/0293594 A1 | 12/2006 | Redel |
| 2007/0088416 A1 | 4/2007 | Atalar et al. |
| 2007/0276226 A1* | 11/2007 | Tal ................. G06T 7/0026 600/424 |
| 2010/0056378 A1* | 3/2010 | Timinger ............ H01F 6/02 505/162 |

FOREIGN PATENT DOCUMENTS

| | | |
|---|---|---|
| WO | 2005022185 A1 | 3/2005 |
| WO | 2006026548 A1 | 3/2006 |
| WO | 2007073576 A1 | 7/2007 |

OTHER PUBLICATIONS

Gupta, et al., Simulation of Elevated T-Waves of an ECG Inside a Static Magnetic Field (MRI), IEEE Transactions on Biomedical Engineering, 2008, 55(7):1890-1896.

Schmidt, et al., MRI-Compatible 12-lead ECG: Improved MHD Suppression, Ischemia Monitoring, and Non-Invasive Cardiac Output, Proc. Intl. Soc. Mag. Reson. Med., 2009, ISMRM 4778.

PCT International Search Report and Written Opinion, Application No. PCT/US2012/033883, dated Aug. 2, 2012, 7 pages.

Anami, et al., Stepping Stone Sampling for Retrieving Artifact-Free Electroencephalogram During Functional Magnetic Resonance Imaging, NeuroImage, 2003, 19:281-295.

Laufs, et al., Recent Advances in Recording Electrophysiological Data Simultaneously with Magnetic Resonance Imaging, NeuroImage, 2008, 40:515-528.

\* cited by examiner

SYSTEM AND METHOD FOR ACQUIRING PATIENT PHYSIOLOGICAL INFORMATION DURING AN MRI SCAN

CROSS-REFERENCE TO RELATED APPLICATIONS

This application represents the national stage entry of PCT International Application No. PCT/US2012/033883 filed on Apr. 17, 2012 and claims priority to U.S. Provisional Application No. 61/477,528 filed Apr. 20 2011, and U.S. Provisional Application No. 61/478,281 filed Apr. 22, 2011, all of which are hereby incorporated by reference herein in their entirety and for all purposes.

BACKGROUND OF THE INVENTION

The field of the invention is medical devices and methods for their use. More particularly, the invention relates to physiological monitoring of a patient, such as electrocardiogram monitoring, electro-anatomic mapping, and electro encephalography (EEG), during a medical imaging process.

The electrocardiogram (ECG) is a widely used clinical tool for cardiac physiological monitoring and for the real-time diagnosis of heart conditions. Surface ECG monitoring, in which the ECG electrodes are attached to a patient's skin, is one type of ECG monitoring that is often used with medical imaging processes. Frequently, patients with cardiac conditions will undergo, for example, a magnetic resonance imaging (MRI) scan in which ECG information is monitored during the scan sequence and used to assist in MRI image acquisition. The ECG information that is obtained may be used, for example, for properly synchronizing cardiac MRI scans, which is a process typically referred to as "gating." Because cardiovascular anatomy is continuously moving throughout the MRI scan, synchronization or "gating" of MRI data acquisition with the cardiac cycle allows for improved imaging of the cardiovascular anatomy at the various phases of the cardiac cycle. Surface ECG monitoring is also frequently used for physiological monitoring of patients who are being scanned for multiple indications (brain, knee, abdomen, etc.), or who are undergoing therapeutic interventions inside the MRI (even interventions not within the cardiovascular system). This is especially true for patients who are anesthetized during the scan or who have a history of heart disease or of stroke.

Surface ECG monitoring inside an MRI scanner presents several challenges that can affect the quality, and thus the usability, of the ECG signals and MRI data acquired. First, the ECG electrodes can experience unwanted voltages that are induced during the ramping up and down of the magnetic field gradients used in the MRI scan. Due to the changing magnetic field caused by the gradient rampings, electric charges induced in the ECG electrodes can have amplitudes up to a few volts. Other voltages can be induced in the ECG electrodes by system control signals sent to the scanner, such as those used to bias diodes in radio-frequency excitation coils prior to radio-frequency transmission. The above induced voltages can be many times larger than the voltage levels of the true ECG signals and, therefore, can saturate the ECG acquisition equipment, making the true ECG signals more difficult to accurately filter out and detect. In addition, the higher voltages can potentially damage the ECG acquisition equipment, which is configured to ordinarily detect only measurements in the range of a few milli-volts. Additionally, the induced voltages can have a frequency content of anywhere between about 100-10,000 Hz, which can render it difficult to remove the unwanted induced signals with simple frequency-based filters. Similarly, the ECG electrodes and leads may conduct radio frequency (RF) fields, such as 64 MHz for 1.5 T or 127 MHz for 3 T, which are induced into the ECG electrodes and leads by the MRI scan sequence's RF pulses. These RF-induced signals cause further noise and, thus, also deteriorate the quality of the signals acquired by the ECG electrodes. Not only do these phenomena negatively affect the acquisition of ECG information, they can interfere with acquiring the desired imaging data.

Attempts have been made to address the issues confronting use of surface ECG monitoring inside an MRI scanner, but have met with only limited success. Most attempted solutions have simply taken the approach of using a smaller number of ECG electrodes (typically around 3 to 5 electrodes) that are closely distanced from each other in order to, in theory, reduce the induced RF and gradient voltages. However, 12-lead ECG surface monitoring arrangements, in which electrodes are placed at designated positions on the torso, is the preferred and most widely used system for monitoring heart condition. Reducing the number of electrodes to only 3 to 5, and arranging the electrodes much more closely than the standard 12-lead arrangement, causes the quality and usefulness of the ECG signals to be severely deteriorated. As a result, such approaches are useful only to perform MRI scan synchronization and do not provide physiological monitoring-quality ECG traces.

Other attempted solutions have involved the use of software filtering or digital signal processing of the acquired ECG signals to remove or suppress the RF and gradient induced components in the ECG leads, but these have met with limited success and also do not provide physiological monitoring-quality traces. Noise caused by gradient ramping and RF transmission during an MRI scan sequence is intrinsically a difficult problem to address with software and digital signal processing, because the gradient noise component in ECG leads can be on the order of a thousand times stronger than the true ECG signal component. In addition, because the gradient fields applied by MR systems constantly change to a significant degree in terms of magnitude, direction, frequency, and duration (due to different requirements of each imaging sequence), it is difficult or impossible for signal-processing algorithms to adapt to the large variety of potential gradient noise.

Electro-Anatomic-Mapping (EAM) is a relatively newer clinical tool than traditional surface ECG monitoring, in which ECG data is collected at various positions inside the body, including on the walls of the cardiac chambers. One of the distinguishing differences from surface ECG monitoring is that positional information is also acquired, sometimes on the same conductive lines as the ones that transfer the ECG signals from the electrodes to the receiver. This positional information is acquired, for example, by inducing electrical currents from surface electrodes and sampling them using catheters that have multiple electrodes on their shaft and that are moved inside the body. The positional tracking signals are generally electromagnetic signals at higher frequencies (5-10 kHz) than those found in conventional ECG (0-300 Hz), so they are easily separated by the EAM receiver. The common practice is to display the position of the catheter electrodes and the ECG voltage at those points, which defines the EAM map. Available EAM systems include the NavX® systems offered by St. Jude Medical, Inc. and the CarTo systems offered by Biosense Webster, Inc.

However, like surface ECG monitoring, EAM mapping inside an MRI scanner also presents several issues that can affect signal quality. First, the ECG component of EAM signals encounters the same RF and gradient induced noise problems as discussed above. Second, the positional localization component of the EAM signals suffer from the induced voltages caused by the gradient ramps as well, since the noise created by the gradient ramps is within the same reception band (5-10 kHz) of the localization voltages. For example, one type of NavX® system operates using a 5.8 kHz signal, while others operate with 8 kHz signals.

These issues confronting the use of EAM inside an MRI scanner have either not been addressed at all, or have only been addressed by an unsatisfactory solution. In fact, the only techniques currently in accepted use that offer positional information in MRI scanners are either based on passive tracking (i.e., using the MRI images themselves for following interventional devices) or use MRI techniques for active tracking (e.g., MR-tracking or MRI-gradient tracking). These solutions do not work outside the MRI scanner, so they cannot be used to monitor a patient during transfer in and out of the scanner, during portions of the procedure that are conducted outside the MRI bore, or during periods in which the patient is inside the scanner, but no images are being acquired.

Moreover, the issues confronting acquisition of ECG and EAM information during an MRI scan can also negatively impact the use of other physiological monitoring tools, such as pulse oximeters, blood pressure cuffs, and respiratory monitors. Each of these clinical tools may include the use of electrodes and leads that can also be susceptible to the same unwanted currents and voltages induced by gradient ramping and RF transmission occurring during an MRI scan.

It would therefore be desirable to provide a system and method for reducing or avoiding the negative effects of RF and gradient induced voltages on ECG and EAM signals (and other physiological monitoring signals), to allow for acquisition of physiological monitoring-quality ECG and/or EAM signals from inside an MRI scanner during a scan. Similarly, it would be further desirable if the system and method allowed for acquisition of such signals both inside and outside the scanner, as well as both during periods in which images are being acquired and when they are not being acquired.

SUMMARY OF THE INVENTION

The present invention overcomes the aforementioned drawbacks by providing a system that includes circuits for disconnecting output of physiological monitoring devices during periods of an MRI scan sequence that can induce unwanted voltages in the monitoring devices or otherwise cause noise in the output of the devices, while permitting communication of the devices' output during other periods of the scan sequence. In particular, the system utilizes a signal gating switch circuit that is responsive to control signals from components of the MRI system that are responsible for causing the induced voltages and/or noise.

It is an aspect of the invention to provide an MRI system that comprises a magnet system, a plurality of gradient coils, an RF system, a patient monitoring system, and a control circuit. The magnet system is configured to generate a polarizing magnetic field about all or part of a patient arranged in the MRI system, the gradient coils are configured to apply a gradient field to the polarizing magnetic field, and the RF system is configured to apply an excitation field to the subject and acquire resulting MR image data. The patient monitoring system is arranged to acquire a physiological condition of the patient and to communicate signals representative of the physiological condition, such as ECG signals and/or EAM signals. The control circuit is configured to coordinate acquisition of the physiological condition signals during a scan with operation of either or both of the gradient coils and the RF system.

It is another aspect of the invention to provide a patient monitoring system that includes at least one electrode configured to sense physiological information from a patient and an MRI scanner interface configured to receive signals from an MRI scanner concerning operation of at least one of a gradient system and an RF system of the MRI scanner The patient monitoring system also includes a control circuit connected to receive signals from the electrode(s) and to regulate use of the output of the electrode(s) during an MRI scan. In the system, regulation by the control circuit is controlled according to the signals received by the MRI scanner interface.

It is a further aspect of the invention to provide a method for acquiring patient physiological information during an MRI scan. The method includes the steps of receiving signals concerning operation of a gradient system and/or an RF system of an MRI scanner during a scan sequence, receiving patient monitoring signals acquired by a physiological monitoring device at least partially arranged inside the MRI scanner during the scan sequence, and coordinating operation of the physiological monitoring device based on the signals concerning operation of the at least one of a gradient system and an RF system of an MRI scanner, to at least one of impede receipt of the patient monitoring signals during a portion of the scan sequence and disregard patient monitoring signals during the portion of the scan sequence.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
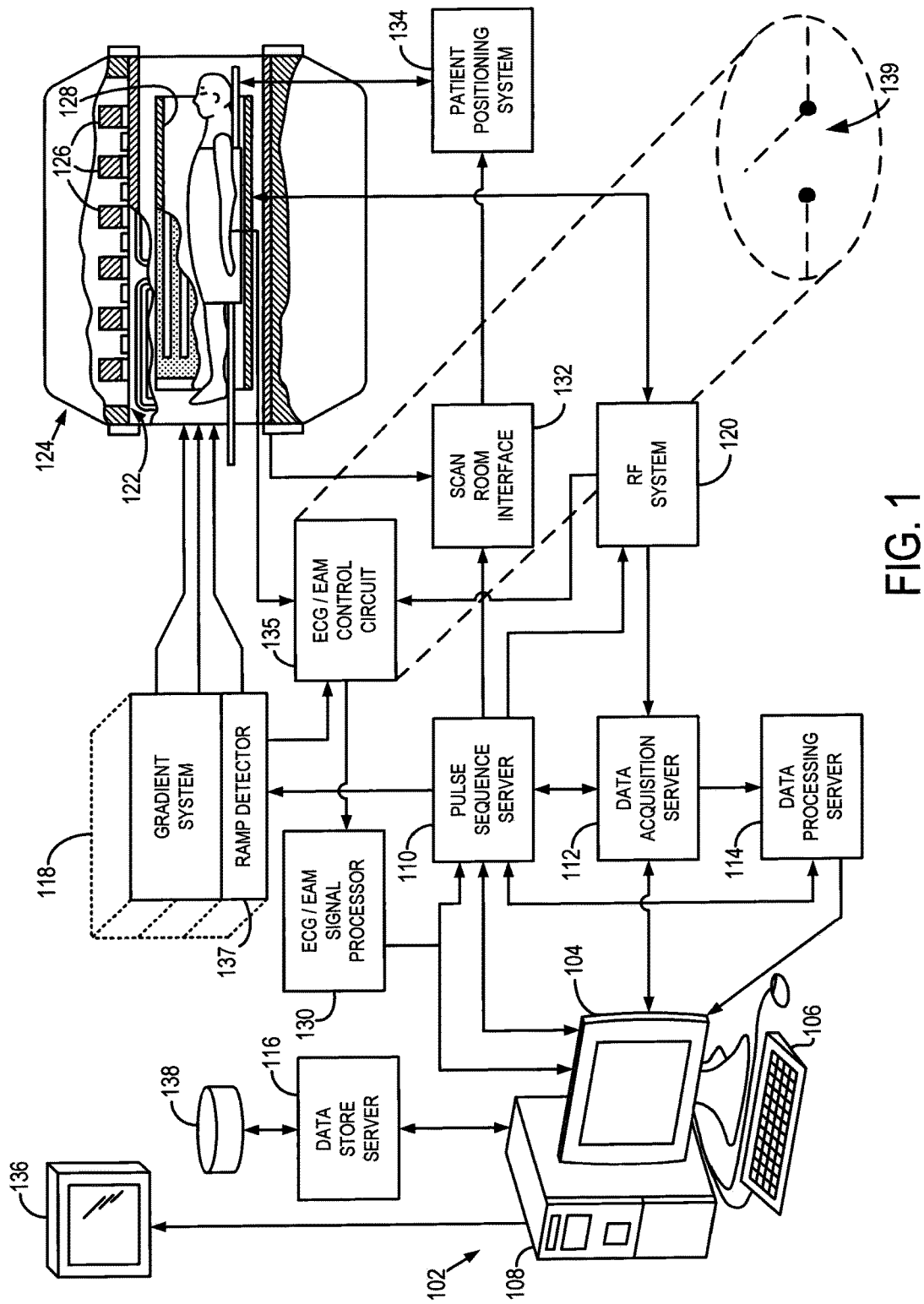
FIG. 1 is a block diagram of an exemplary magnetic resonance imaging ("MRI") system in which ECG/EAM signal gating control and processing circuits are integrated with the MRI system in accordance with the present invention.

Referring particularly to FIG. 1, the present invention is employed in a magnetic resonance imaging ("MRI") system. The MRI system includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system. The workstation 102 is coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radio frequency ("RF") system 120. Gradient waveforms necessary to perform the prescribed scan are produced and applied to the gradient system 118, which excites gradient coils in a gradient coil assembly 122 to produce the magnetic field gradients $G_x$, $G_y$, and $G_z$ used for position encoding MR signals. The gradient coil assembly 122 forms a part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RE coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \quad \text{Eqn. (1);}$$

and the phase of the received MR signal may also be determined:

$$\phi = \tan^{-1}\left(\frac{Q}{I}\right). \quad \text{Eqn. (2)}$$

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. The data acquisition server 112 may also be employed to process MR signals used to detect the arrival of contrast agent in a magnetic resonance angiography ("MRA") scan. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a back projection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 104 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

In some scans, the pulse sequence server 110 may optionally receive physiological patient monitoring signals from a number of different sensors connected to the patient, such as ECG, EEG, or EAM signals from electrodes and associated interventional catheters, pulse oximeter signals, signals from a blood pressure cuff, or respiratory signals from a bellows or other respiratory monitoring device. In the embodiment depicted in FIG. 1, ECG, EEG, or EAM signals are acquired from a patient inside the MRI scanner during a scan and are transmitted via an ECG/EAM control circuit 135 to an ECG/EAM signal receiver or processor 130. Preferably, the ECG or EAM signals are conducted using low-noise cables, to reduce interference inside the scan room. The processor 130 conditions, filters, and/or processes the raw signals and ultimately transmits ECG and/or EAM information to the workstation 102 and/or the pulse sequence server 110. Alternatively, the functionality of the processor 130 may be integrated with the workstation 102 or other component of the MRI system, or may include a commercial ECG or EAM receiving and processing system such as, for example, a Cardiolab-IT Electrophysiology Recording System offered by GE Healthcare or the NavX® system offered by St. Jude Medical, Inc.

The signal gating control circuit 135 may be responsive to a variety of control signals to coordinate ECG and EAM acquisition with operation of gradient system 118 and RF system 120. As discussed above, the ramping up and down of the gradient fields as well as certain RF transmissions can seriously degrade the quality of output from ECG and EAM electrodes, as well as other physiological monitoring devices. Thus, during periods of an imaging sequence that cause induced voltages and noise in the output of the ECG and EAM electrodes (such as gradient ramping and RF transmission), output from the ECG and EAM electrodes can be disconnected or discarded by control circuit 135 so as to limit the effect of the unwanted noise on patient monitoring and MRI image acquisition. For example, in the embodiment shown, control circuit 135 is responsive to gating signals from the RF system 120 and a gradient ramp detection circuit 137 integrated with the gradient system 118. These gating signals may be, for example, TTL (transistor-transistor logic) signals used to cause the control circuit 135 to alternately disconnect the output of the electrodes from the processor 130 or connect the output of the electrodes to the processor 130.

Accordingly, signal gating control circuit 135 may comprise a switch that alternately opens to disconnect or impede output of the ECG or EAM electrodes and closes to communicate output of the electrodes to processor 130, in according with control signals from the gradient system 118 and RF system 120. Such a switch may include solid-state, fast-response electronics to ensure a rapid disconnection and reconnection of the real-time ECG or EAM acquisition during and after the gradient ramps. Desirable switching delay times are less than 200 nsec, although it is understood that other switching times may be acceptable. In one embodiment, the switch could comprise a single pole double throw electronic switch. Thus, as depicted in FIG. 1, control circuit 135 may include a switch 139 connected between the patient electrodes and the processor 130.

Alternatively, as will also be discussed below with respect to FIG. 2, control circuit 135 may include a system for discarding or ignoring signals output by the electrodes (or other physiological monitoring tool) during periods of induced noise (such as during gradient ramping or RF transmission). In such an implementation, software algorithms may be used that analyze control signals from the gradient system 118 and RF system 120 as timing signals to blank, discard, or ignore ECG or EAM acquisition during periods of induced noise. Such software may be executed on processor 130, or the functionality of control circuit 135 and processor 130 may both be integrated with workstation 104 or other computational component of the MRI system. Alternatively, control circuit 135 may comprise a software algorithm that is implemented by a digital signal processing circuit for removing output from the electrodes during periods of induced noise from the signal transmission stream to the processor 130. In other words, control circuit 135 may include a switch, circuit, chip, or software algorithm for preventing use of signals output by patient physiological condition sensors during periods of noise induced by operation of the gradient system 118 and/or RF system 120 during an MRI scan.

The gradient ramp detection circuit 137, which provides a control signal to control circuit 135, may be integrated with the gradient system 118 by being installed in the gradient cabinet as a separate circuit or may be included as part of the functionality of the gradient system 118 itself. In an alternative configuration, the gradient ramp detection circuit 137 may include a pickup coil positioned within the bore of the magnet assembly 124. The ramp detection circuit 137 is connected to a real-time output of the gradient system 118, so that the detection circuit 137 can monitor application of gradient fields during a scan sequence and output a signal to the control circuit 135 causing it to interrupt or disconnect output of the patient monitoring electrodes whenever the gradient field is being ramped up or ramped down. As discussed above, it is the ramping stages of gradient field application which can cause induced voltages in ECG and EAM electrodes. Thus, during steady state "on" and fully "off" stages of gradient field application, the gradient ramp detection circuit 137 outputs a signal to the control circuit 135 causing it to connect or communicate the output of the patient monitoring electrodes to the processor 130.

Likewise, the RF system 120 may also be connected to, or include, a detection circuit (not shown), but control of signal gating control circuit 135 according to operation of the RF system may simply be achieved using existing output lines of the RF system. For example, in many MRI systems, an unblank signal is output by the RF amplifier of the RF system 120 just prior to and/or during RF transmission which could also be used for control of the control circuit 135.

Alternatively, the signal gating control circuit 135 may be responsive to signals from the scan prescription workstation 102, or the pulse sequence server 110 that indicate when the gradient system will be ramping up or down and/or when the RF system will be transmitting. The control circuit 135 may also be responsive to the presence of other noise-causing signals that are related to or accompany the operation of the gradient and/or RF system. For example, in certain GE MRI scanners, a 1000V signal is sent to the RF body coil to reverse bias the diodes on it, prior to the actual RF signal being sent from the RF amplifier. This 1000V signal can also create substantial noise within the bore of the magnet, such as in ECG and EAM electrodes, so the control circuit 135 can also disconnect output from such electrodes during application of the 1000V signal. In addition, the control circuit 135 may also be responsive to a simple user override. Furthermore, as stated above, the control circuit 135 may also gate the output of other physiological monitoring tools, such as pulse oximeters, blood pressure cuffs, respiratory monitors, and the like, which may also experience induced voltages and noise from gradient and RF operation during an MR scan.

Once the gated output of the ECG or EAM electrodes reaches the processor 130, the processor 130 then communicates the gated ECG or EAM information to the pulse sequence server 110 and/or workstation display 104. Thus, the gated information can be used for displaying an ECG trace or an EAM image, as will be described in more detail below, and for MR image acquisition. That is, for cardiac-gated scans, pulse sequence server 110 can synchronize, or "gate," the performance of the scan with the subject's heart beat or respiration. In other embodiments, the control circuit 135 may communicate ECG signals directly to the pulse sequence server 110 instead of, or in addition to, communication to the processor 130.

Figure 2:
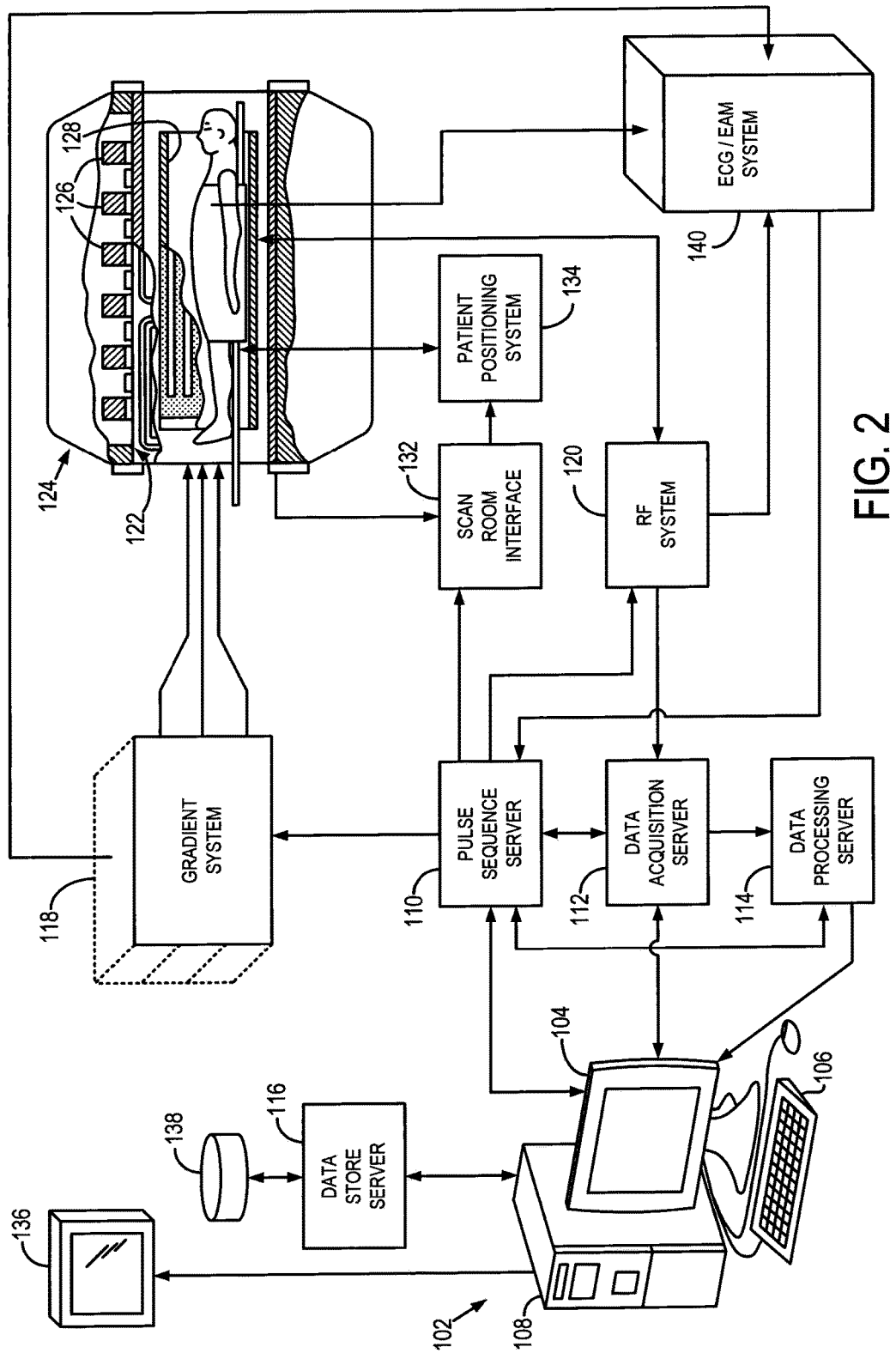
FIG. 2 is a block diagram of an exemplary magnetic resonance imaging ("MRI") system employed in combination with an exemplary ECG/EAM system in accordance with the present invention.

Referring now to FIG. 2, an additional embodiment is shown in which a separate, stand-alone ECG or EAM system 140 is employed in conjunction with a standard MRI system. The stand-alone system 140 may include, for example, a portable ECG unit offered by such companies as GE Healthcare, Siemens Healthcare, Philips Healthcare, Cardiac Science, Medrad, and Invivo. Using this arrangement, patient monitoring can seamlessly continue (1) outside of, and apart from, the MRI system, (2) inside the MRI system when no scanning is taking place, and (3) inside the MRI system during an MRI scanning sequence. In this embodiment, the gradient ramp detection circuit, the ECG/

EAM signal gating control circuit, and the ECG/EAM receiver or processor are all integrated into the stand-alone system 140.

During operation, the ECG/EAM system 140 is connected via an MRI scanner interface to output lines of the gradient system 118 and the RF system 120, to allow the internal gradient ramp detection circuit and signal gating control circuit to prevent or disregard ECG/EAM acquisition at the proper times. Thus, within the stand-alone ECG or EAM system 140, a chip or circuit may be included for detecting periods of gradient ramping in real time and sending control signals to a signal gating control switch or circuit that connects or disconnects ECG/EAM acquisition in coordination with the detected periods of gradient ramping. Likewise, a chip or circuit may be included for detecting periods of RF transmission, or receiving signals indicating that RF transmission is taking place or about to take place, in real time, and sending control signals to a signal gating control switch or circuit that connects or disconnects ECG/EAM acquisition in coordination with the periods of RF transmission. Alternatively, the ECG/EAM system 140 may include software that allows the system to receive input regarding operation of the gradient system 118 and RF system 120, calculate periods of gradient ramping and/or RF transmission, then ignore output from the ECG/EAM electrodes during those periods. In either case, the MRI system may be adapted or retrofit to include simple, removable connection points for plug-in leads so that the signals regarding operation of the gradient system 118 and RF system 120 may be communicated to the ECG/EAM system 140. Alternatively, the ECG/EAM system 140 may simply be connected to the pulse sequence server 110 or workstation 104 to receive information concerning the pulse sequence prescriptions for the gradient and RF systems.

Figure 3:
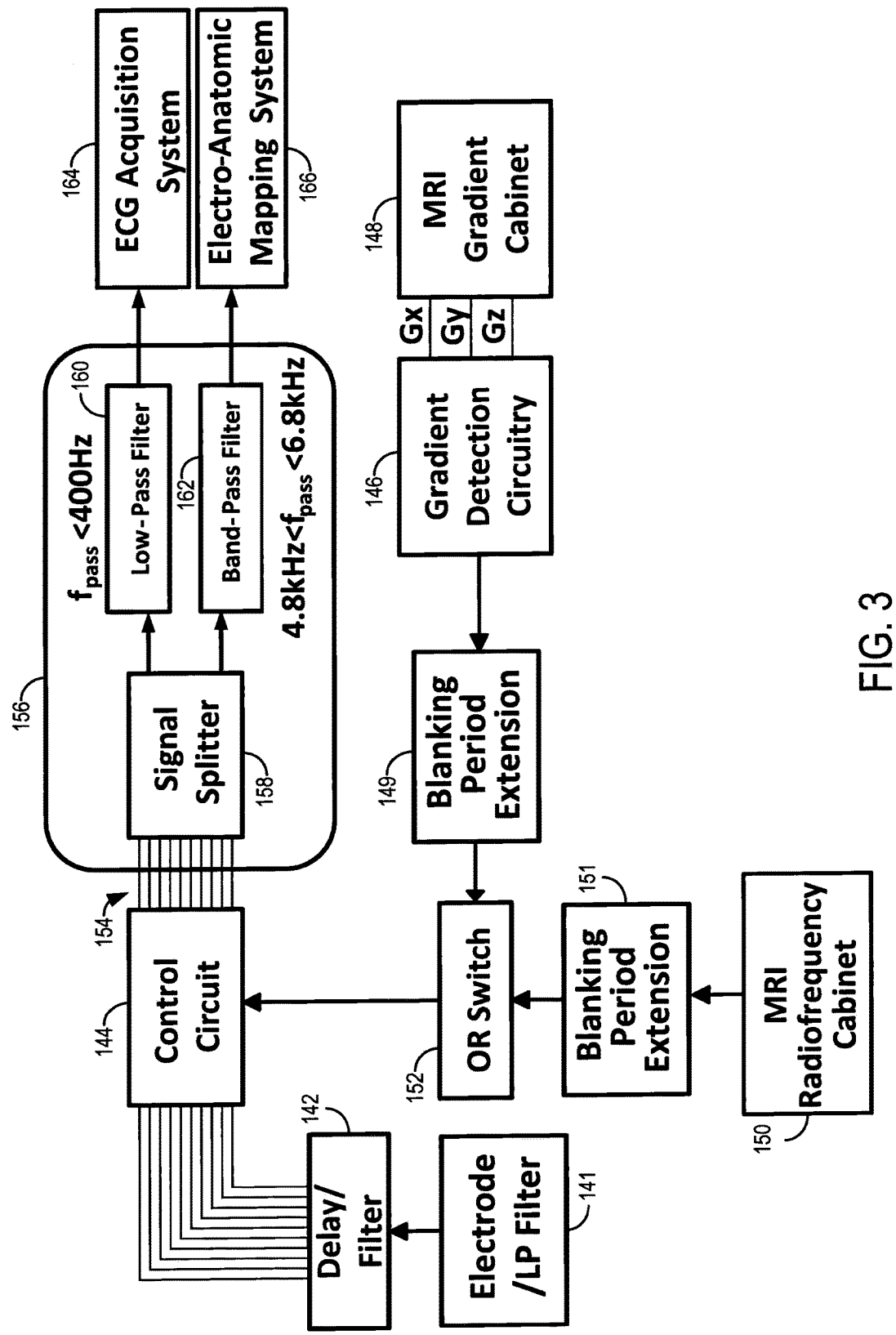
FIG. 3 is a block diagram of a representative ECG/EAM switching and processing circuit in accordance with the present invention.
Figure 4A:
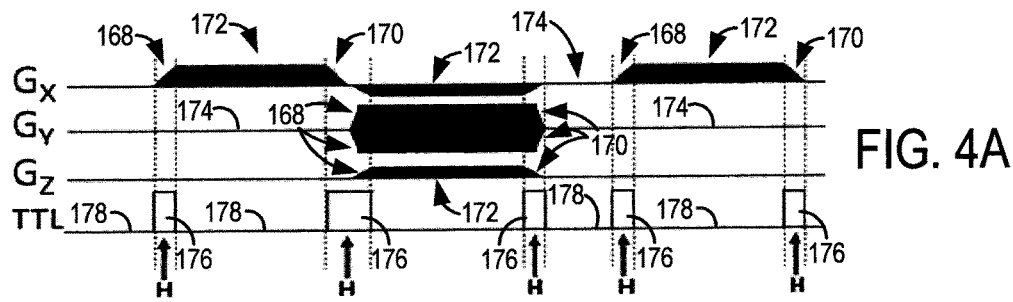
FIG. 4 is a chart depicting gradient waveforms from an exemplary MRI scan and exemplary ECG traces.
Figure 4B:
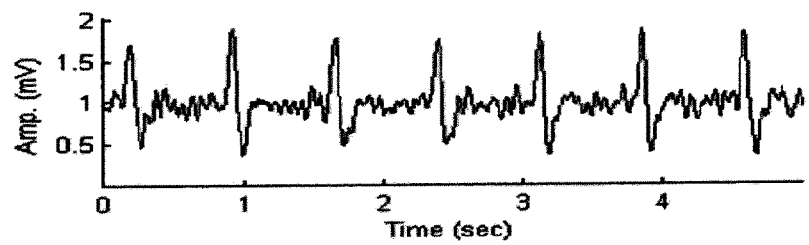
Figure 4C:
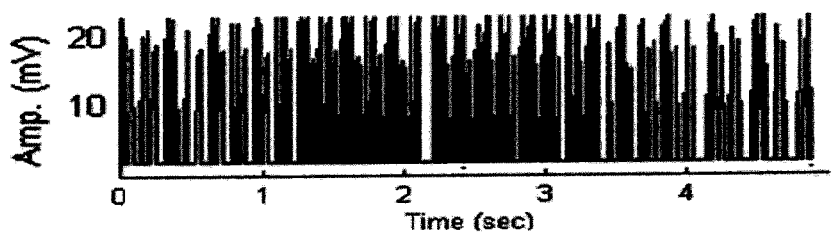
Figure 4D:
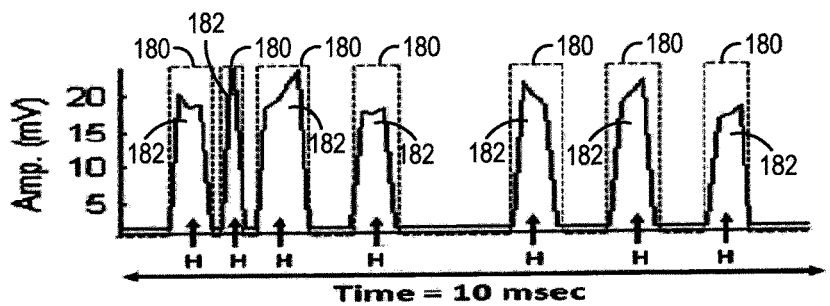
Figure 4E:
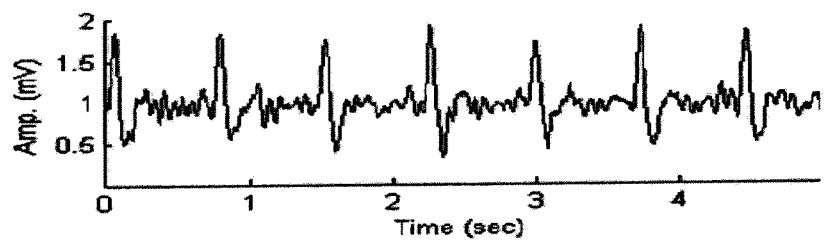

Referring now to FIG. 3, a functional block diagram is shown, which depicts the operation and interconnection of certain aspects of the above-described embodiments in greater detail. In FIG. 3, a plurality of electrodes 141, for example, a set of ECG or EAM electrodes and/or associated catheters (not shown), are connected through a delay/filter 142 to one or more signal gating control circuits 144, illustrated in FIG. 3 as SPDT switches. The delay/filter 142, which may include a low-pass filter can be used to delay signals from the electrodes 141 before arriving at the control circuits 144 by several tens of microseconds, for example, approximately 40 microseconds. This delay allows, for example, the illustrated SPDT switches to react fast enough, even if a triggering pulse arrives a little late. That is, triggering, such as the above described TTL output, is turned ON when a gradient in the X, Y, or Z direction is slewed to a new value. Without such a delay there is the chance of some short spike, for example 20 microseconds in duration, of noise may get through the SPDT switch before it cuts off transmission. In addition, the low-pass filter broadens somewhat any very-rapid spikes. It also works as an anti-aliasing filter for the A/D converters in ECG or EAM recording systems. Similarly to the gradient detection circuitry 146 and associated blanking period extension 149, signals may be acquired from an MRI RF cabinet 150 through an associated blanking period extension 151. Thus, these two blanking extensions 149, 151, which may both be variable with independent control, provide greater control over the switching and allow for control over associated delays.

For ECG-only systems, these lines will contain ECG signals, which generally are on the order of a few milli-volts at a few hundred Hz. For EAM systems, these lines may contain ECG signals as well as positional signals at a few kHz.

As discussed above, single pole double throw (SPDT) switches may be used to gate the communication of the electrodes' output. In the embodiment depicted in FIG. 3, the control circuits 144 are responsive to control signals from the MRI RF system 150 and MRI gradient system 148. (However, as discussed above, a software or signal processing approach may be taken in lieu of, or even in combination with, a switch, to disregard physiological condition acquisition during periods of induced noise. In addition, a digital or analog "sample and hold" circuit may be used in a complement to the control circuits 144 in order to replace the disregarded signal, and supply the acquisition system, with data acquired immediately before the switch disconnects). The gradient detection circuit 146 is employed to monitor gradient waveforms output by the gradient system 148 in real time to determine periods when gradient fields in the X, Y, or Z direction are being ramped up or ramped down. The blanking period extension or blanking circuit 149 may be included. The blanking extension, which may be variable in duration, allows the TTL pulse reactions to be extended by a variable amount of time, for example, 0-6 milliseconds, if there is still some MRI noise that would otherwise go through the switch after it reopened. A circuit having an OR switch 152 may be used to perform an "OR" function, allowing the switches to be disconnected whenever gradient ramping is occurring OR when RF transmission is occurring. This "OR" switch 152 may be integrated with the control circuits 144 and/or both circuits may be integrated into a stand-alone ECG or EAM system. Also, the control circuits 144 may be formed by two or more SPDT circuits arranged in series, for example, to behave like an "OR," but without the OR switch. As discussed above, however, an "OR" functionality is not necessarily required, since embodiments of the invention may gate electrode output according to only one noise-inducing MR function (e.g., gating according to only gradient ramping, according to only RF transmission, or according to only some other MR function like 1000V diode biasing signals). Note that the invention also embodies the possibility of placement of delay lines and/or signal filters before control circuits 144. Such delay lines allow for removing components of the large voltages that may occur somewhat (several microseconds) before the OR switch 152 sends a command to the control circuits 144 to disconnect signal transmission, since these delay lines delay the arrival of the large signals until the switch is activated.

Downstream of the control circuits 144, the gated electrode outputs 154 are communicated to a receiver/processor 156 during periods of the MRI scan sequence at which no gradient fields are being ramped up or down (i.e., all X, Y, and Z gradients are either at a steady state "on" or are fully "off") and/or no RF transmission is taking place. Thus, the control circuits 144 (or, in other embodiments, a signal gating software algorithm or digital signal processing circuit) prevent the receiver/processor 156 from using output of the ECG or EAM electrodes that was affected by noise caused by induced voltages.

In an EAM system, as shown, the receiver/processor 156 includes a signal splitter 158 to split each gated electrode output 154. One of the split signals for each gated electrode output 154 is then sent through a low-pass filter 160 to separate out the ECG component of the electrode output 154, while the other split signal is sent through a band-pass filter 162 to separate out the EAM positional component of the electrode output 154. In an ECG-only system, though a signal splitter 158 is not necessary, it may be still be desirable to use a low pass filter 160 to reduce stray noise, for example a minimum-phase low pass Butterworth filer. These filtering steps may be performed digitally in either a workstation or in the processing unit of an ECG/EAM unit (such as a GE Cardiolab unit).

The receiver/processor 156 also includes, or is connected to, an ECG acquisition system 164 and/or an EAM system 166. Because the electrodes' output has been gated in coordination with operation of the gradient system 148 and RF system 150, the output that is communicated to receiver/ processor 156 and ECG acquisition system 164, 166 does not include gradient-induced noise. Accordingly, an ECG acquisition system 164 (such as a GE Healthcare Cardiolab-IT system) can sample only gradient and RF noise-free ECG signals, and display physiological monitoring-quality images of ECG traces. These images may be displayed on a screen of a stand-alone ECG unit, on the screen of an MRI system workstation, or both. Likewise, an EAM system 166 can sample only gradient and RF noise-free EAM positional signals, and can thus display full electrophysiological images without distortion or complication from gradient or RF noise. Correspondingly, because the output of the ECG/ EAM electrodes is gated so as to reduce the effect of induced voltages, a full set of electrodes can be utilized in a normal monitoring arrangement, such as, for example, a standard 12-lead electrode arrangement. In other words, there is no longer a need to reduce the number of electrodes or the spacing of the electrodes to attempt to limit the amount of induced noise, because the periods of acquisition in which noise is induced by gradient ramping or RF transmission are gated or ignored. Also, a "sample and hold circuit" can be added to the system. This circuit may be a digital memory storage circuit that continuously acquires data into a circular buffer to feed prior-acquired data to the receiver/processor 156 during periods when signal transmission from the electrodes to is blocked. Alternatively, the "sample and hold circuit" can be comprised of analog components such as a capacitor placed between the physiologic signal and ground, and located between control circuit 144 and receiver/processor 156. Advantageously, the positional and ECG data is constantly sent to the receivers/processors, although it may introduce some bias into the data.

In addition to preventing induced voltages in electrode outputs from affecting image quality, the control circuits 144 can also be used for another purpose in EAM systems. During operation of an EAM system, some electrodes are used to transmit electric signals that are detected and sampled by electrodes in interventional catheters located inside a patient anatomy, such as a heart chamber. Because the transmission and reception of these electric signals can experience interference from the gradient and RF transmissions inside an MRI scanner, the control circuits144 can also be used to prevent electrodes from transmitting during a gradient ramping period or an RF transmission period. In this case, the control circuits144 would be gated according to the same control signals, and would still be connected to electrode leads, but the transmission of signals on the leads would be travelling in the opposite direction—to the patient from the receiver/processor 156, rather than from the patient to the receiver/processor 156. Likewise, preventing transmission of electric signals from EAM electrodes during certain portions of an MRI scan sequence also reduces the risk that the electric signals from the EAM electrodes could be picked up by the RF coil of the MRI scanner and affect image data acquisition of the MRI system.

Referring now to FIG. 4, a set of graphs 4A-4E of exemplary gradient waveforms and ECG signals is depicted to illustrate certain aspects of the invention. Graph 4A shows a set of waveforms Gx, Gy, and Gz representing the timing and amplitude of gradient fields applied in the X, Y, and Z directions inside an MRI scanner during a scan sequence. As can be seen, the gradients are usually applied such that they have trapezoidal waveforms, with periods of ramping up 168 and periods of ramping down 170 between steady state "on" periods 172 and fully "off" periods 174. The bottom line of graph 4A depicts an exemplary "TTL" control signal which experiences a high level 176 whenever a gradient field in any direction is ramping up or ramping down, and a low level 178 at all other times. This control signal represents the output of a gradient ramping detection circuit, as described above, which is used to cause a signal gating switch to open (high levels 178) and close (low levels 178) according to the gradient ramping waveforms.

Graph 4B is an exemplary ECG signal acquired when no MRI scan sequence is taking place. Graph 4C, in contrast, is an exemplary ECG signal acquired during an MRI scan, with no gating or other approach to compensate for induced voltages in the ECG electrodes. Graph 4D is a close-up view of a segment of FIG. 4C, with an exemplary TTL control signal (Graph 4A) superimposed thereon. As can be seen, periods 180 when gradient ramping is taken place (as identified by high TTL levels "H") cause false spikes 182 to be seen in the ECG signal.

Graph 4E is an exemplary ECG signal acquired during an MRI scan sequence, using the gradient gating aspects of the invention described above. As can be seen, especially in comparison to Graph 4C, the ECG signal is far less affected by induced voltages, and is of a quality that can be easily used for normal physiological monitoring (e.g., the QRS points of the ECG trace can be accurately and easily determined).

The present invention has been described in terms of one or more preferred embodiments, and it should be appreciated that many equivalents, alternatives, variations, and modifications, aside from those expressly stated, are possible and within the scope of the invention.

The invention claimed is:

1. A magnetic resonance imaging (MRI) system comprising:
   a magnet system configured to generate a polarizing magnetic field about at least a portion of a patient arranged in the MRI system;
   a plurality of gradient coils configured to apply a gradient field to the polarizing magnetic field;
   a radio frequency (RF) system configured to apply an excitation field to the subject and acquire MR image data therefrom;
   a patient monitoring system arranged to acquire a physiological condition of the patient and to communicate signals representative of the physiological condition;
   a control circuit including a switching circuit, the control circuit configured to coordinate acquisition of the signals representative of the physiological condition by the patient monitoring system with operation of at least one of the gradient coils and the RF system, and the switching circuit configured to disconnect acquisition of the signals representative of the physiological condition by the patient monitoring system during periods of at least one of gradient ramping and RF transmission.

2. The MRI system as recited in claim 1 in which the patient monitoring system includes at least ECG electrodes and the signals representative of the physiological condition include at least ECG signals.

3. The MRI system as recited in claim 2 in which the patient monitoring system includes a standard 12-lead ECG electrode arrangement.

4. The MRI system as recited in claim 1 further comprising a gradient ramping detection circuit configured to output a control signal to the control circuit during gradient ramping periods of a scan, to cause the control circuit to prevent communication of the signals representative of the physiological condition by the patient monitoring system during gradient ramping periods.

5. The MRI system as recited in claim 4 in which the gradient ramping detection circuit is integrated with a gradient system of the MRI system.

6. The MRI system as recited in claim 4 further comprising an ECG unit, and wherein the gradient ramping detection circuit is integrated with the ECG unit.

7. The MRI system as recited in claim 1 in which the patient monitoring system is further configured to generate images derived from the signals representative of the physiological condition, including a physiological monitoring-quality ECG graph determined from the gated ECG signals.

8. The MRI system as recited in claim 1 in which the coordinated acquisition of the signals representative of the physiological condition by the patient monitoring system is communicated to a pulse sequence server configured to acquire MR image data.

9. The MRI system as recited in claim 1 in which the control circuit configured to coordinate acquisition of the signals representative of the physiological condition comprises a processing unit of the MRI system programmed to implement a software algorithm for disregarding the signals acquired during periods of at least one of gradient ramping and RF transmission.

10. A patient monitoring system comprising:
   at least one electrode configured to sense physiological information from a patient and output signals indicative thereof;
   an MRI scanner interface configured to receive signals from an MRI scanner concerning operation of at least one of a gradient system and an RF system of the MRI scanner;
   a control circuit including a switching circuit, the control circuit connected to receive signals from the at least one electrode and to regulate use of the output of the at least one electrode during an MRI scan, the switching circuit configured to alternately communicate and disconnect output of the at least one electrode during periods of noise from voltages induced by the at least one of a gradient system and an RF system; and
   wherein regulating by the control circuit is controlled according to the signals received by the MRI scanner interface.

11. The patient monitoring system as recited in claim 10 in which the patient monitoring system comprises at least one of a stand-alone ECG monitoring unit and a stand-alone EAM unit.

12. The patient monitoring system as recited in claim 10 in which the MRI scanner interface comprises a gradient ramping detection circuit configured to determine periods during which the gradient system of the MRI scanner is ramping up or down and to output a control signal to the control circuit to cause the circuit to not communicate output from the at least one electrode during the ramping periods.

13. The patient monitoring system as recited in claim 10 in which the MRI scanner interface communicates control signals to the control circuit to cause the control circuit to not communicate output of the at least one electrode during periods of RF transmission of the MRI scanner.

14. The patient monitoring system as recited in claim 10 wherein the MRI scanner interface comprises a connector for removably engaging with at least one of a workstation associated with the MRI scanner, a pulse sequence server associated with the MRI scanner, the gradient system, or the RF system, to receive the signals concerning operation of the at least one of a gradient system and an RF system.

15. The patient monitoring system as recited in claim 10 wherein the at least one electrode further comprises a set of EAM electrodes, and wherein the switching circuit is further connected to prevent the EAM electrodes from transmitting signals during operation of the at least one of the gradient system and the RF system.

16. The patient monitoring system as recited in claim 10 further comprising a filter to separate ECG signals and EAM signals from output of the at least one electrode, and wherein the processor is further configured to output an ECG graph and an EAM image to at least one of a display integrated with the patient monitoring system and a display associated with the MRI scanner, based on user preference.

17. The patient monitoring system as recited in claim 10 in which the control circuit comprises a processing unit programmed to disregard output of the at least one electrode during periods of noise from voltages induced by the at least one of the gradient system and the RF system.

18. A method for acquiring patient physiological information during an MRI scan comprising:
   receiving signals concerning operation of at least one of a gradient system and an RF system of an MRI scanner during a scan sequence;
   receiving patient monitoring signals acquired by a physiological monitoring device at least partially arranged inside the MRI scanner during the scan sequence; and
   coordinating operation of the physiological monitoring device based on the signals concerning operation of the at least one of a gradient system and an RF system of an MRI scanner, to at least one of impede receipt of the patient monitoring signals during a portion of the scan sequence and disregard patient monitoring signals during the portion of the scan sequence.

* * * * *